US012673905B1

(12) United States Patent
Ghiassi et al.

(10) Patent No.: US 12,673,905 B1
(45) Date of Patent: Jul. 7, 2026

(54) THRUSTER PROPELLANTS

(71) Applicant: Government of the United States, as represented by the Secretary of the Air Force, Wright-Patterson AFB, OH (US)

(72) Inventors: Kamran B. Ghiassi, Palmdale, CA (US); Levi Michael Joseph Moore, Lancaster, CA (US); Michael R. Natisin, Palmdale, CA (US); Kevin T. Greeson, Lancaster, CA (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 1482 days.

(21) Appl. No.: 16/415,071

(22) Filed: May 17, 2019

Related U.S. Application Data

(60) Provisional application No. 62/835,067, filed on Apr. 17, 2019.

(51) Int. Cl.

| | |
|---|---|
| ***C06B 43/00*** | (2006.01) |
| ***B64G 1/40*** | (2006.01) |
| ***C07D 209/04*** | (2006.01) |
| ***C07D 209/44*** | (2006.01) |
| ***C07D 233/54*** | (2006.01) |
| ***C07D 235/04*** | (2006.01) |

(52) U.S. Cl.
CPC ................ *C06B 43/00* (2013.01); *B64G 1/40* (2013.01); *C07D 209/04* (2013.01); *C07D 209/44* (2013.01); *C07D 233/54* (2013.01); *C07D 235/04* (2013.01)

(58) Field of Classification Search
None
See application file for complete search history.

(56) References Cited

U.S. PATENT DOCUMENTS

| | | | |
|---|---|---|---|
| 3,789,608 | A | 2/1974 | Free |
| 6,516,604 | B2 | 2/2003 | Mojarradi et al. |
| 7,932,492 | B2 | 4/2011 | Demmons et al. |
| 8,791,411 | B2 | 7/2014 | Lozano et al. |
| 9,638,178 | B1 | 5/2017 | Courtney et al. |

(Continued)

OTHER PUBLICATIONS

Skalicky, M.; Marketa Rybackova, M.; Kysilka, O.; Kvicalova, M.; Cvacka, J.; Cejka, J.; Kvicala, J.; Synthesis of bis(polyfluoroalkylated)imidazolium salts as key intermediates for fluorous NHC ligands. Journal of Fluorine Chemistry 2009, 130, 966-973.

(Continued)

*Primary Examiner* — Aileen B Felton
(74) *Attorney, Agent, or Firm* — AFMCLO/JAZ; Richard M. Mescher

(57) ABSTRACT

The present invention relates to thruster propellants, processes of making thruster propellants and space vehicles comprising thrusters that employ such propellants. The disclosed thruster propellants are advantageous because do not readily uptake water and are conductive. Furthermore, when compared to previous thruster propellants they have a higher mass, a higher density and/or a lower surface tension. Thus, when used in a thruster, such propellants can generate equal or higher thrust than previous thruster propellants.

12 Claims, 8 Drawing Sheets

(56) References Cited

U.S. PATENT DOCUMENTS

| | | | | |
|---|---|---|---|---|
| 2004/0073054 A1* | 4/2004 | Zhang | C07D 491/10 | 568/683 |
| 2004/0245406 A1* | 12/2004 | Guiheen | F02K 9/563 | 244/169 |
| 2011/0070486 A1* | 3/2011 | Matsumoto | H01M 8/1016 | 252/62.2 |

OTHER PUBLICATIONS

Mirjafari, A.; O'Brien, R.A.; Murray, S.M.; Mattson, K.M.; Mobarrez, N.; West, K.N.; Davis Jr., J.H.; Lipid-Inspired Ionic Liquids Containing Long-Chain Appendages: Novel Class of Biomaterials with Attractive Properties and Applications. American Chemical Society Ionic Liquids: Science and Applications ACS Symposium Series 2012, Chapter 9, 199-216.

Coffman, C.; Perna, L.; Li, H.; Lozano, P.C.; On the Manufacturing and Emission Characteristics of a Novel Borosilicate Electrospray Source. Joint Propulsion Conferences 2013, 1-12.

Courtney, D.G.; Dandavino, S.; Shea, H.; Comparing Direct and Indirect Thrust Measurements from Passively Fed Ionic Electrospray Thrusters. Journal of Propulsion and Power 2016, vol. 32, No. 2, 392-407.

Dandavino, S.; Ataman, C.; Ryan, C. N.; Chakraborty, S.; Courtney, D.; Stark, J. P. W.; Shea, H.; Microfabricated electrospray emitter arrays with integrated extractor and accelerator electrodes for the propulsion of small spacecraft. J. Micromech. Microeng. 2014, 24, 1-13.

O'Brien, R.A.; Mirjafari, A.; Jajam, V.; Capley, E. N.; Stenson, A. C.; West, K. N.; Davis Jr., J. H.; Functionalized ionic liquids with highly polar polyhydroxylated appendages and their rapid synthesis via thiol-ene click chemistry. Tetrahedron Letters 2011, 52, 5173-5175.

Mirjafari, A.; lonic liquid syntheses via click chemistry: expeditious routes toward versatile functional materials. Chem. Commun., 2018, 54, 2944-2961.

Lozano, P. C.; Wardle, B. L.; Moloney, P.; Rawal, S.; Nanoengineered thrusters for the next giant leap in space exploration MRS Bulletin 2015, 40, 842-849.

Schadt, K.; Kerscher, B.; Thomann, R.; Mulhaupt, R.; Structured Semifluorinated Polymer Ionic Liquids for Metal Nanoparticle Preparation and Dispersion in Fluorous Compartments. Macromolecules 2013, 46, 4799-4804.

Murray, S. M.; O'Brien, R. A.; Mattson, K. M.; Ceccarelli, C.; Sykora, R. E.; West, K. N.; Davis, Jr., J. H.;. The Fluid-Mosaic Model, Homeoviscous Adaptation, and Ionic Liquids: Dramatic Lowering of the Melting Point by Side-Chain Unsaturation. Angew. Chem. Int. Ed. 2010, 49, 2755 -2758.

Mirjafari, A.; O'Brien, R. A.; West, K. N.; Davis, Jr., J. H.; Synthesis of New Lipid-Inspired Ionic Liquids by Thiol-ene Chemistry: Profound Solvent Effect on Reaction Pathway. Chem. Eur. J. 2014, 20, 7576-7580.

John K. Ziemer, J. K.; Gamero-Castaño, M.; Hruby, V.; Spence, D.; Demmons, N.; McCormick, R.; Roy, T.; Colloid Micro-Newton Thruster Development for the ST7-DRS and LISA Missions. AIAA 2005, 4265, 1-9.

* cited by examiner

THRUSTER PROPELLANTS

RIGHTS OF THE GOVERNMENT

The invention described herein may be manufactured and used by or for the Government of the United States for all governmental purposes without the payment of any royalty.

CROSS-REFERENCE TO RELATED APPLICATIONS

This application claims the benefit of priority under 35 U.S.C. §119(e) to U.S. Provisional Application Serial No. 62/835,067 entitled "THRUSTER PROPELLANTS" filed on Apr. 17, 2029. The content of which is expressly incorporated herein by reference in its entirety.

FIELD OF THE INVENTION

The present invention relates to thruster propellants, processes of making thruster propellants and space vehicles comprising thrusters that employ such propellants.

BACKGROUND OF THE INVENTION

Space vehicles use thrusters to change their velocity and/or trajectory. Such thrusters require a propellant that can provide propulsive force from which such velocity and/or trajectory changes arise. Current thrusters typically apply an electrical charge that causes molecules of thruster propellant to be ejected from the space vehicle thus generating such propulsive force. Unfortunately, current propellants absorb water as they are hydroscopic which dilutes the thruster propellant, increases the electrical energy required to produce the propulsive force and, due to water out gassing during operation, can short the thruster electrodes which results in thruster failure. Furthermore, current thruster propellants do not provide the duration and level of thrust that is desired.

Applicants recognized that the source of the aforementioned water absorption problem lie in the specific combination of anions and cations found in current thruster propellants. While not being bound by theory applicants believe that the current anions and cations are smaller and thus closer together and behave more like traditional simple salts which are soluble in water. To solve such problem, Applicants attached a hydrophobic fluorinated tail to the current cations. While not being bound by theory, Applicants believe that such fluorination provides a synergistic, hydrophobicity when compared to similar hydrophobic tails that lack said fluorination. In addition to recognizing the source of the water absorption problem, Applicants recognized that the source of the aforementioned duration and thrust level problem lie in the lack of mass of current thruster propellants as well as the density of such propellants. In short, Applicants recognized that in order to improve the overall performance of a thruster propellant, the propellant's mass had to increase without significantly decreasing the density. Applicants solved such problem by the aforementioned fluorination of the thruster propellants' cations.

SUMMARY OF THE INVENTION

The present invention relates to thruster propellants, processes of making thruster propellants and space vehicles comprising thrusters that employ such propellants. The disclosed thruster propellants are advantageous because they do not readily uptake water and are conductive. Furthermore, when compared to previous thruster propellants they have a higher mass and/or a higher density. Thus, when used in a thruster, such propellants can generate equal or higher thrust than previous thruster propellants.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

Figure 1:
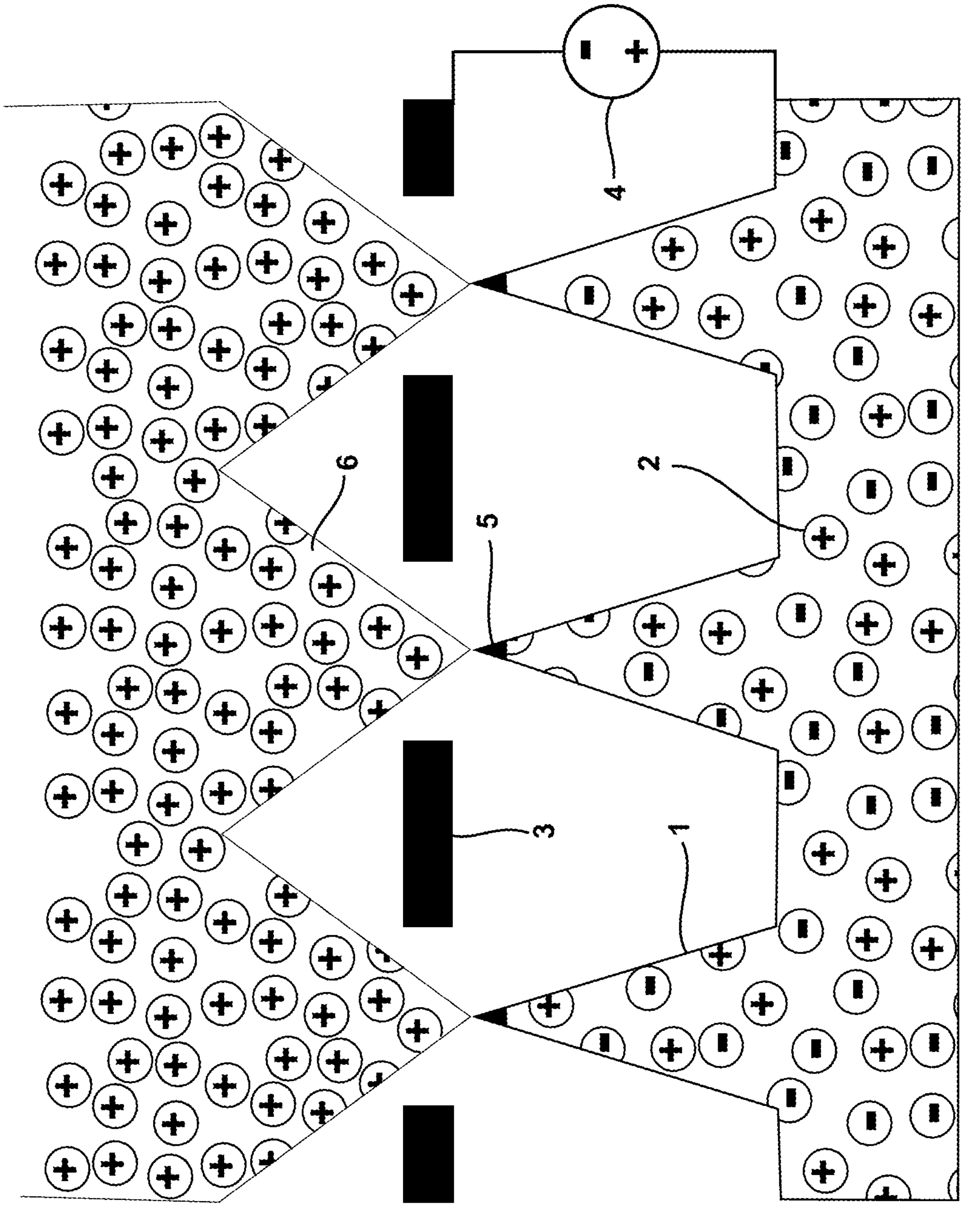
FIG. 1 is a schematic displaying the underlying principles of operation of a passively-fed porous media liquid ion electrospray thruster.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Definitions

As used herein, the term "ionic liquid" when referring to the thruster propellants of present invention means a material that can exist as a liquid at at least one temperature in the range of minus 150 Celsius to 300 Celsius and that is made of ions while a liquid.

Unless specifically stated otherwise, as used herein, the terms "a", "an" and "the" mean "at least one".

As used herein, the terms "include", "includes" and "including" are meant to be non-limiting.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Thruster Propellants and Spacecraft Comprising Same

For purposes of this specification, headings are not considered paragraphs and thus this paragraph is Paragraph 0046 of the present specification. The individual number of each paragraph above and below this paragraph can be determined by reference to this paragraph's number. In this paragraph 0046, Applicants disclose a thruster propellant comprising a plurality of cations and anions, and having an overall net zero charge, said cation comprising one or more heads, and one or more hydrophobic fluorinated tails that comprise one or more sulfur atoms, said sulfur atoms being separated from said fluorination and said head group by at least one carbon, said one or more tails being covalently bound to said one or more heads, each of said one or more heads being independently selected from the group consisting of an imidazolium, an imidazolinium, a phosphonium, an ammonium, a sulfonium, a pyridinium, a pyrrolidinium.

Applicants disclose the thruster propellant of Paragraph 0046 wherein each of said one or more tails is an aliphatic moiety connected to one or more sulfur atoms which are each then connected to a partially hydrogenated fluorinated carbon chain, preferably each of said one or more tails is independently selected from the group consisting of tails having Formula 1 or Formula 2 below wherein:

a) S is sulfur;
b) F is fluorine;
c) X is hydrogen or fluorine;
d) the indice a is an integer from 0 to 20, preferably the indice a is an integer from 2 to 12, more preferably the indice a is an integer from 2 to 4, most preferably the indice a is 3;
e) the indice b is an integer from 1 to 10, preferably the indice b is an integer from 1 to 8, more preferably the indice b is an integer from 1 to 3, most preferably the indice b is 2;
f) the indice c is an integer from 1 to 18, preferably the indice c is an integer from 1 to 8, more preferably the indice c is an integer from 6 to 8, most preferably the indice c is 8;
g) the indice d is an integer from 1 to 14, preferably the indice d is an integer from 1 to 10, more preferably the indice d is an integer from 1 to 4, most preferably the indice d is 1; and
h)  represents an attachment point for Formulas 1 and 2 below to the thruster propellant Formula 1

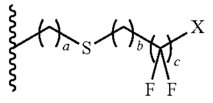

Formula 2

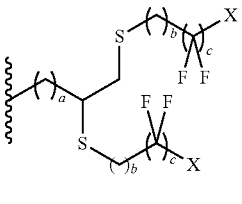

Applicants disclose the thruster propellant of Paragraphs 0046 through 0047 comprising one or more organic linking groups that link one or more of said one or more heads, preferably each of said one or more linkers being independently selected from the group consisting of aliphatic, aromatic, poly(ether), (poly)thio(ether), and isocyanurate.

Applicants disclose the thruster propellant of Paragraphs 0046 through 0048, said thruster propellant comprising a material selected from Formulas 3 through 14 below and mixtures thereof:

wherein for each of Formulas 3 through 14:

a) each anion A is independently selected from the group consisting of tetrafluoroborate, hexafluorophosphate, and bis(trifluoromethylsulfonyl)azanide;

b) each $R_1$ is independently selected from the group consisting of: hydrogen; Formula 1 wherein the indice a is an integer from 1 to 20, preferably the indice a is an integer from 2 to 12, more preferably the indice a is an integer from 2 to 4, most preferably the indice a is 3 and all the other limitations of Formula 1 are as specified in Paragraph 0047; Formula 2 wherein the limitations of Formula 2 are as specified in Paragraph 0047; a $C_1$-$C_{12}$ branched alkane; a $C_1$-$C_{12}$ linear alkane; a substituted aromatic moiety; or an unsubstituted aromatic moiety, preferably said substituted aromatic moiety is a substituted benzene moiety and said unsubstituted aromatic moiety is a benzene moiety;

c) each $R_2$, $R_3$ and $R_4$ is independently selected from the group consisting of; hydrogen; Formula 1 wherein the limitations of Formula 1 are as specified in Paragraph 0047; Formula 2 wherein the limitations of Formula 2 are as specified in Paragraph 0047; a $C_1$-$C_{12}$ branched alkane; a $C_1$-$C_{12}$ linear alkane; a substituted aromatic moiety; or an unsubstituted aromatic moiety, preferably said substituted aromatic moiety is a substituted benzene moiety and said unsubstituted aromatic moiety is a benzene moiety, with the proviso that for Formula 3, Formula 5 and Formula 6, adjacent $R_3$ and $R_4$ moieties can be one or more benzo moieties rather than single independent moieties.

d) indice e for each Formulas 10 through 14 is independently from 1 to 3 Examples of Formula 3, Formula 5 and Formula 6, molecules comprising such benzo moieties are depicted by Formulas 10 through 14 wherein indice e for each formula is independently from 1 to 3.

e) each $R_5$ is independently selected from the group consisting of: hydrogen; Formula 1 wherein the indice a is an integer from 1 to 20, preferably the indice a is an integer from 2 to 12, more preferably the indice a is an integer from 2 to 4, most preferably the indice a is 3 and all the other limitations of Formula 1 are as specified in Paragraph 0047; a $C_1$-$C_{12}$ branched alkane; a $C_1$-$C_{12}$ linear alkane; a substituted aromatic moiety; and an unsubstituted aromatic moiety, preferably said substituted aromatic moiety is a substituted benzene moiety and said unsubstituted aromatic moiety is a benzene moiety;

Formula 3

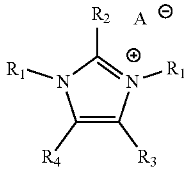

Formula 4

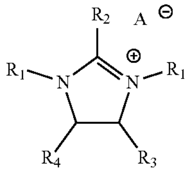

-continued

Formula 5

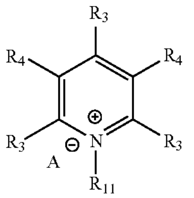

Formula 6

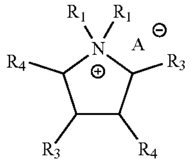

Formula 7

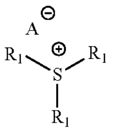

Formula 8

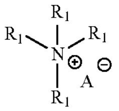

Formula 9

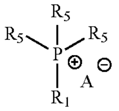

Formula 10

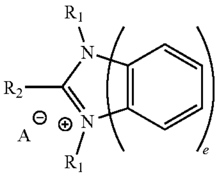

Formula 11

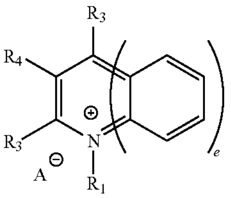

Formula 12

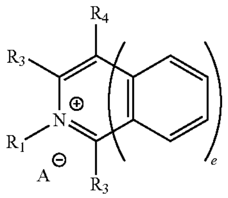

Formula 14

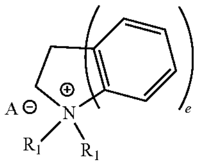

Applicants disclose the thruster propellant of Paragraph 0049 wherein Formula 3's $R_1$ through $R_4$ groups are selected from the following sets:

a) moiety Set 1 wherein:

(i) the $R_1$ adjacent to $R_4$ is methyl;

(ii) the $R_1$ adjacent to $R_3$ is a tail having Formula 1 wherein the indice a is 3, the indice b is 2 and the indice c is 8, X is fluorine; and (iii) $R_2$, $R_3$ and $R_4$ are hydrogen;

b) moiety Set 2 wherein:

(i) $R_1$ is a tail having Formula 1 wherein the indice d is 1, the indice b is 2 and the indice c is 8, X is fluorine;

(ii) $R_2$, $R_3$ and $R_4$ are hydrogen;

c) moiety Set 3 wherein:

(i) the $R_1$ adjacent to $R_4$ is methyl;

(ii) the $R_1$ adjacent to $R_3$ is a tail having Formula 2 wherein the indice d is 1, the indice b is 2 and the indice c is 8, X is fluorine; and (iii) $R_2$, $R_3$ and $R_4$ are hydrogen;

d) moiety Set 4 wherein:

(i) the $R_1$ adjacent to $R_3$ is formula has Formula 15 below wherein the indice f is 10 and $R_6$ is a tail having Formula 1 wherein for said Formula 1, the indice a is 3, the indice b is 2 and the indice c is 8, X is fluorine Formula 15

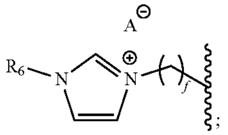

(ii) the $R_1$ adjacent to $R_4$ is a tail having Formula 1 wherein the indice a is 3, the indice b is 2 and the indice c is 8, X is fluorine; and (iii) $R_2$, $R_3$ and $R_4$ are hydrogen;

e) moiety Set 5 wherein:

(i) the $R_1$ adjacent to $R_3$ has Formula 15 below wherein the indice f is 2 and $R_6$ is a tail having Formula 1 wherein for Formula 1, the indice a is 3, the indice b is 2 and the indice c is 8, X is fluorine Formula 15

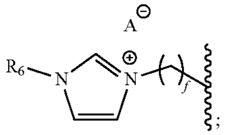

(ii) the $R_1$ adjacent to $R_4$ is a tail having Formula 1 wherein the indice a is 3, the indice b is 2 and the indice c is 8, X is fluorine; and (iii) $R_2$, $R_3$ and $R_4$ are hydrogen.

Process of Making Thruster Propellants

A process of making a thruster propellant, said process comprising subjecting a mixture comprising: a head material, a tail material, a photo initiator; and a solvent to ultraviolent light. Preferably said head material is selected from the group consisting of Formulas 3-15 of Paragraphs 0049 and 0050 of this specification, more preferably said head material has Formula 3 of this specification; preferably said tail material is selected from the group consisting of Formulas 1-2 of Paragraph 0047 of this specification, more preferably said tail material has Formula 1; preferably said photo initiator comprises 2 2-dimethoxy-2-phenylacetophenone; and preferably said solvent is selected from the group consisting of dichloromethane, methanol and mixtures thereof.

The process of Paragraph 0051 wherein said subjecting said mixture to ultraviolent light comprises subjecting said mixture to an ultraviolent light having a power of about 10 to about 100 Watts, preferably subjecting said mixture to ultraviolent light comprises subjecting said mixture to ultraviolent light for a time of from about 1 to 24 hours, preferably for about 1 hour.

Materials and/or their precursors that are needed to produce the thruster propellants disclosed and/or claimed by Applicants in this specification can be purchased from companies such as: MilliporeSigma of St. Louis, MO USA (acquired Sigma-Aldrich), Tokyo Chemical Industry Co., Ltd. having a US office at 9211 North Harborgate Street Portland, OR 97203 USA, and Thermo Fisher Scientific having an address of 168 Third Avenue Waltham, MA USA 02451 (acquired Alfa Aesar and Acros).

Space Vehicles Comprising Thrusters That Employ Propellants

Suitable thrusters that can use the thruster propellants described and claimed herein, include, but are not limited to electrospray thrusters. Preferably such electrospray thrusters are selected from the group consisting of colloid thrusters and ionic liquid electrospray thrusters. Preferably such ionic liquid electrospray thrusters are capillary based ionic liquid electrospray thrusters comprising capillaries that transport thruster propellant from a space vehicle's propellant reservoir to the outside environment thereby providing thrust or porous media electrospray thrusters. Most preferably, such ionic liquid electrospray thrusters are porous media electrospray thrusters. Suitable colloid thrusters are described in U.S. Pat. No. 3,789,608, suitable capillary based ionic liquid electrospray thrusters are described in U.S. Pat. No. 7,932,492 B2, suitable porous media ionic liquid electrospray thrusters are described in U.S. Pat. No. 8,791,411 B1, and U.S. Pat. No. 9,638,178 B1. Suitable space vehicles that can employ the aforementioned thrusters include, but are not limited to satellites, and space stations. Thus, Applicants disclosed a space craft comprising a thruster and a thruster propellant according Paragraphs 0046 through 0050, preferably said propellant is selected from a propellant according to Paragraph 0047, more preferably said propellant is selected from a propellant according to Paragraph 0049, most preferably said propellant is selected from a propellant according to Paragraph 0050; preferably said space craft is selected from a satellite and/or a space station. In one aspect, said satellite is selected from the group consisting of CubeSats, microsatellites, and nanosatellites.

Exemplary Principles of Thruster Operation

The underlying principles of operation of a passively-fed porous media liquid ion electrospray thruster is shown in FIG. 1. Here, a series of sharp features called emitters 1 are fabricated out of a porous material in which the open pore volume has been filled with an ionic liquid 2. Placed directly above the emitters is an extractor electrode 3, which consists of a thin conductive material with openings centered on each emitter to allow extraction and acceleration of the ions from the ionic liquid.

With the geometric arrangement as in FIG. 1, a high-voltage power supply is then used to enforce a potential difference between the extractor electrode and the ionic liquid within the emitters 4. Since the ionic liquid is composed of charged ions, it responds to the electric field produced by this potential difference and is pulled away from the porous emitter surface towards the extractor electrode. With a sufficiently high electric field, an equilibrium between the outward pull of the electric field pressure and the inward pull of the liquid surface tension can be maintained, resulting in the formation of one or more cones of ionic liquid known as Taylor cones 5 at the tip of each emitter. Because the emitter tips act to focus the electric field, sharper emitter tips allow Taylor cone formation at lower voltages.

Once a Taylor cone has been established, further increasing the electric field leads to evaporation of ions and ionic-molecules from the ionic liquid. Once evaporated, the ions are accelerated by the electric field through the extractor apertures and away from the emitters, thus producing thrust 6. As the ions are ejected, capillary forces pull new propellant up through the small pores to the emitters, allowing for a purely passive feed system with no pressure vessels or moving parts. While FIG. 1 shows the emission of positive ions, negative ion emission may be similarly achieved by flipping the high voltage power supply 4 such that the electric field points towards the emitters rather than away from it. Using this technique, the emitted ion polarity may be alternated dynamically to allow charge neutralization and for both species within the ionic liquid propellant to be used.

Figure 2A:
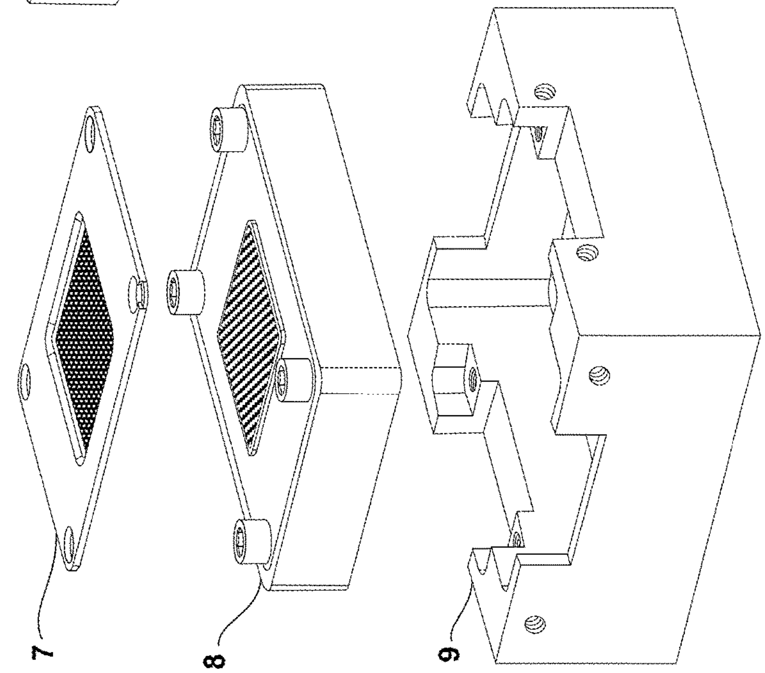
FIG. 2A is an exploded view of a liquid ion electrospray thruster showing the liquid ion electrospray thruster's primary components.
Figure 2B:
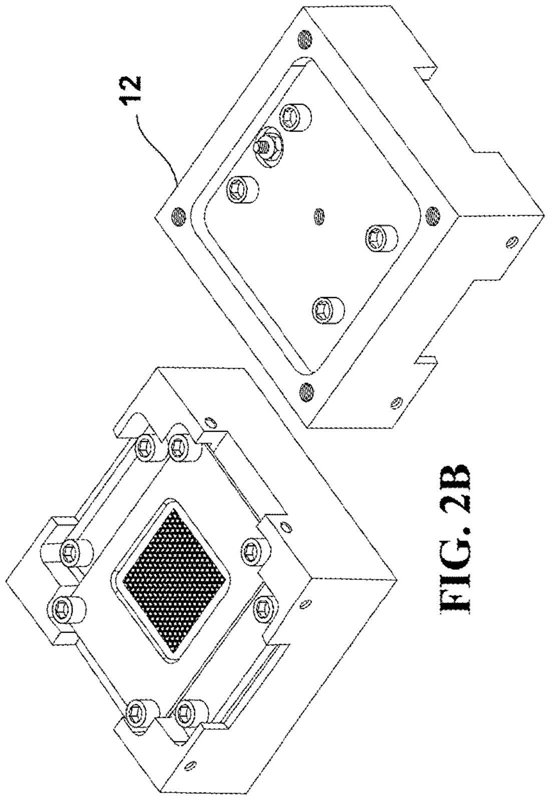
FIG. 2B is a top and bottom isometric view of an assembled liquid ion electrospray thruster.
Figure 2C:
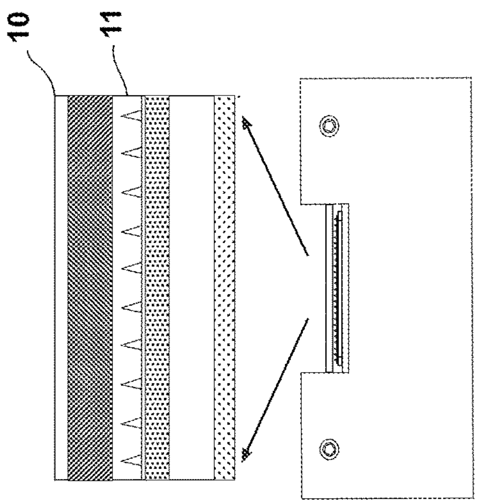
FIG. 2C is a side profile of an assembled liquid ion electrospray thruster.

A non-limiting schematic of one embodiment of a thruster is shown in FIGS. 2A-2C. Referring to FIG. 2A, the primary assemblies of the device are an extractor electrode 7, a multi-component drop-in propellant module 8, and a thruster housing (9). Top and bottom isometric views of a fully assembled unit are shown in FIG. 2B which contains the high voltage connections 12, while FIG. 2C displays a side profile view with the inset showing the extractor and emitter profile in more detail 10. The separation distance between the bottom of the extractor electrode and the tips of the emitters 11 is important. Smaller separations result in lower start-up voltages (i.e., the voltage threshold above which emission occurs), higher thrust produced per power input, and lower ion interception on the extractor grid. For optimal thruster operation this distance should be limited to a few thousandths of an inch or less. This requirement places strict and unique requirements on the fabrication techniques used to construct the various thruster components, as any variability in the emitter heights or extractor electrode flatness will negatively affect thruster performance.

While the primary purpose of the thruster housing is to precisely fix the various components relative to one another, it also serves other important functions. Due to the high voltages required to run the electrospray thruster (typically 1,000 to 3,000 volts), the connections made to the propellant module and extractor electrode is isolated so as to not allow electrical arcing during operation. Additionally, it is best to construct the housing out of a conductive metal such as aluminum to shield the regions outside of the housing from the large potentials inside. In one embodiment of this thruster, a high-voltage pin electrically isolated with ceramic MACOR is connected through the propellant module and thruster housing 12, while the extractor grid is connected through the housing itself, allowing all connection to be made at the rear of the unit so as to not perturb or impede ion emission trajectories.

Figure 3B:
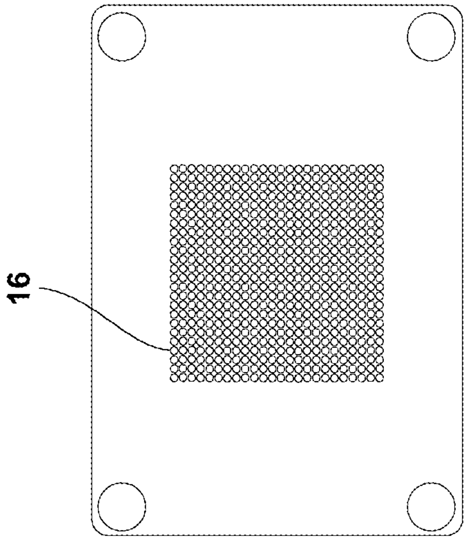
FIG. 3B is a bottom view of a one-piece extractor electrode.
Figure 3A:
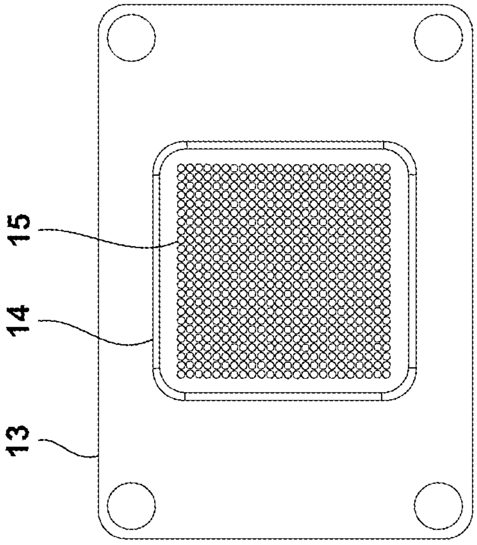
FIG. 3A is a top view of a one-piece extractor electrode.
Figure 3D:
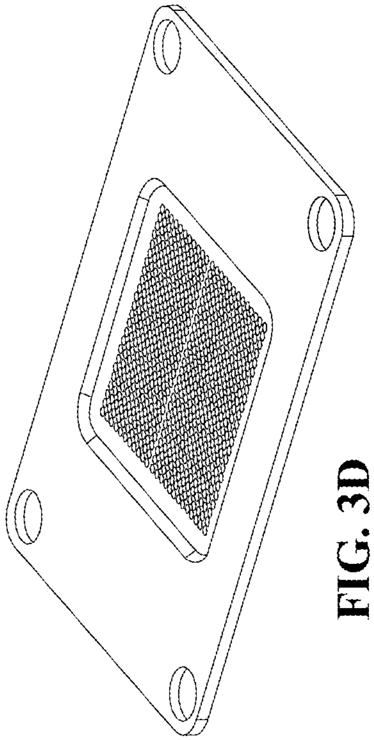
FIG. 3D is an isometric view of a one-piece extractor electrode.
Figure 3C:
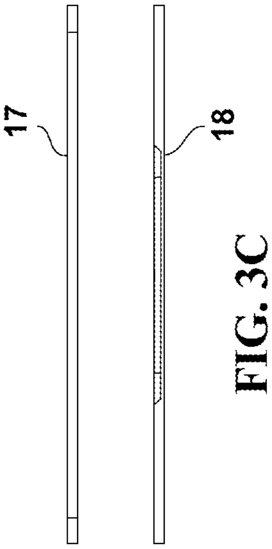
FIG. 3C is a side view of a one-piece extractor electrode.

One embodiment of the extractor electrode in which a one-piece design is used is shown in FIGS. 3A-3D. The active thrust area of the extractor electrode contains many densely packed apertures which enable ion ejection. The holes are typically as large as possible to minimize ion interception, while still maintaining structural integrity. Additionally, the active thrust area is typically no more than a few thousandths of an inch thick to further minimize ion-grid interception. In the embodiment shown in FIG. 3A, a 0.024 inch thick sheet of 316 stainless steel 13 is machined down to 0.003 inch thickness over the active thrust area 14 and contains 576 holes of diameter 0.02 inch spaced 0.0215 inches apart 15. FIG. 3B shows the underside of this embodiment in which it is desired that the material be flat to within a few thousandths of an inch (16) for optimal thruster performance. FIG. 3C shows the side view 17 as well as a cutaway view 18 which shows the thinned down active thrust region. An isometric view is shown in FIG. 3D.

Figure 4A:
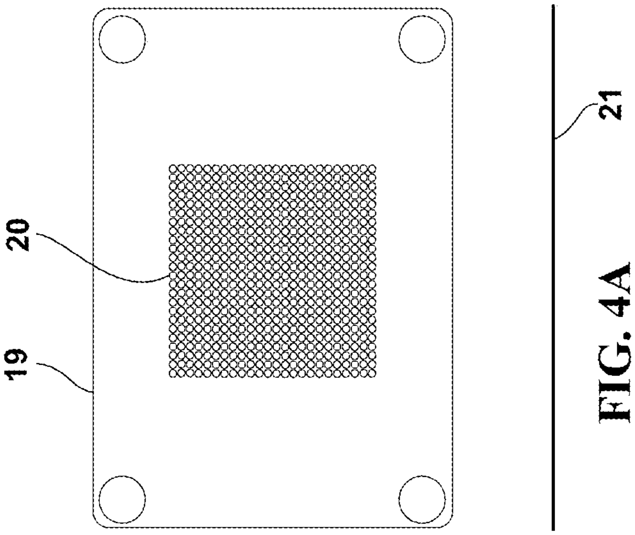
FIG. 4A is a top and side view of a two-piece extractor grid.
Figure 4B:
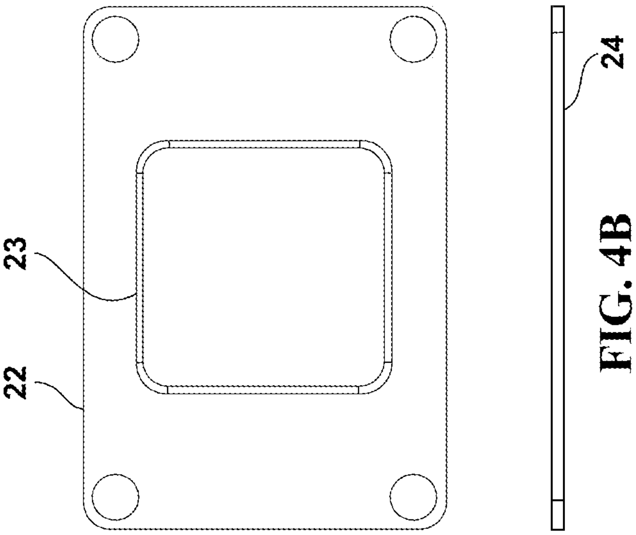
FIG. 4B is a top and side view of a two-piece extractor electrode frame.
Figure 4C:
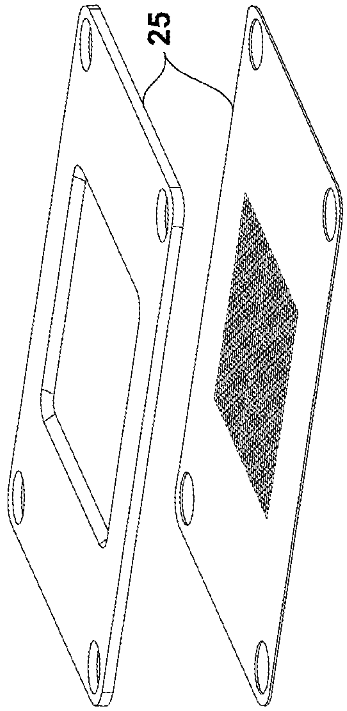
FIG. 4C is an exploded view of a two-piece extractor electrode.
Figure 4D:
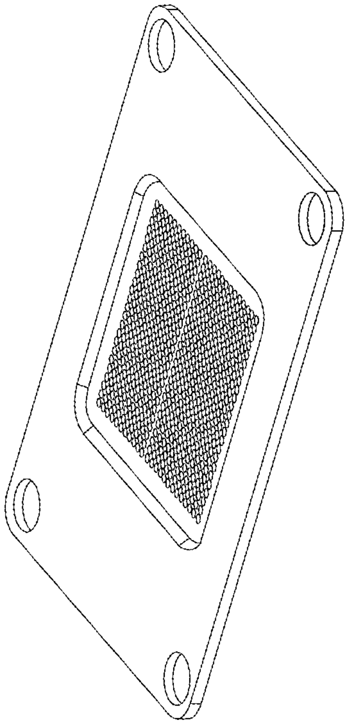
FIG. 4D is an isometric view of an assembled two-piece extractor electrode.

Another embodiment of an extractor electrode is shown in FIGS. 4A-4D. In this case a two-piece design is shown in which a thin molybdenum grid FIG. 4A is bonded to a thicker 316 stainless steel frame FIG. 4B to enforce flatness and rigidity. This design allows materials to be used for the extraction grid in which the machining operations used in the one-piece design shown in FIG. 3A through FIG. 3C are difficult or time-consuming. In FIG. 4A, a 0.003 inch thick sheet of molybdenum 19 and 21 is used as the extraction grid which contains 576 0.02 inch diameter holes 20, while as shown in FIG. 4B a 0.024 inch thick piece of 316 stainless steel 22 and 24 that contains active thrust area opening 23 is used for the frame. FIG. 4C shows the bonding surfaces 25 and FIG. 4D is an isometric view of an assembled two-piece extractor electrode.

Figure 5B:
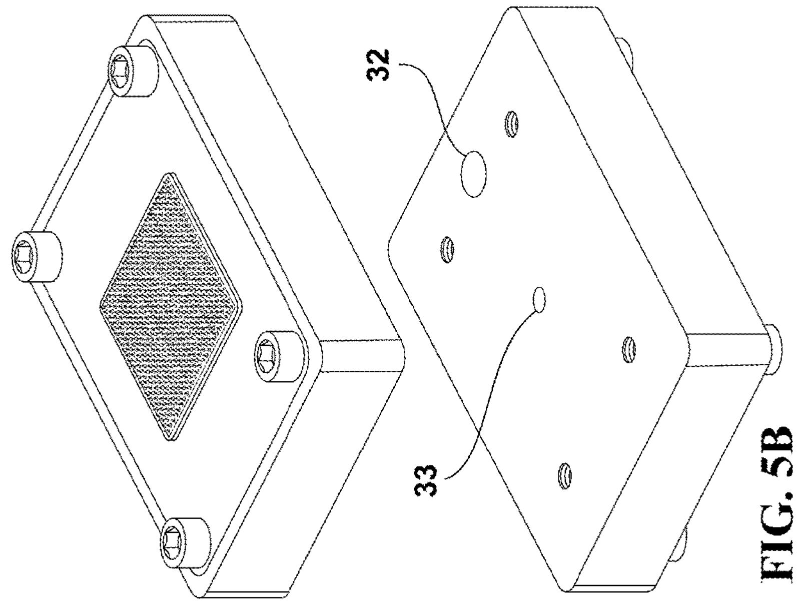
FIG. 5B is a top and bottom isometric view of propellant module.
Figure 5C:
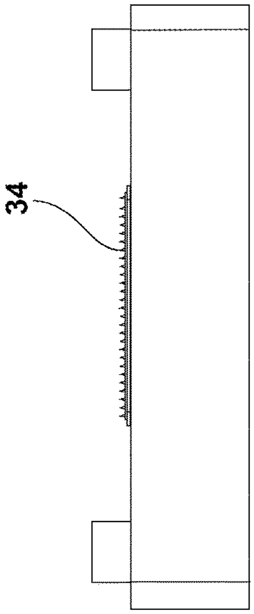
FIG. 5C is a side view of assembled propellant module.
Figure 5A:
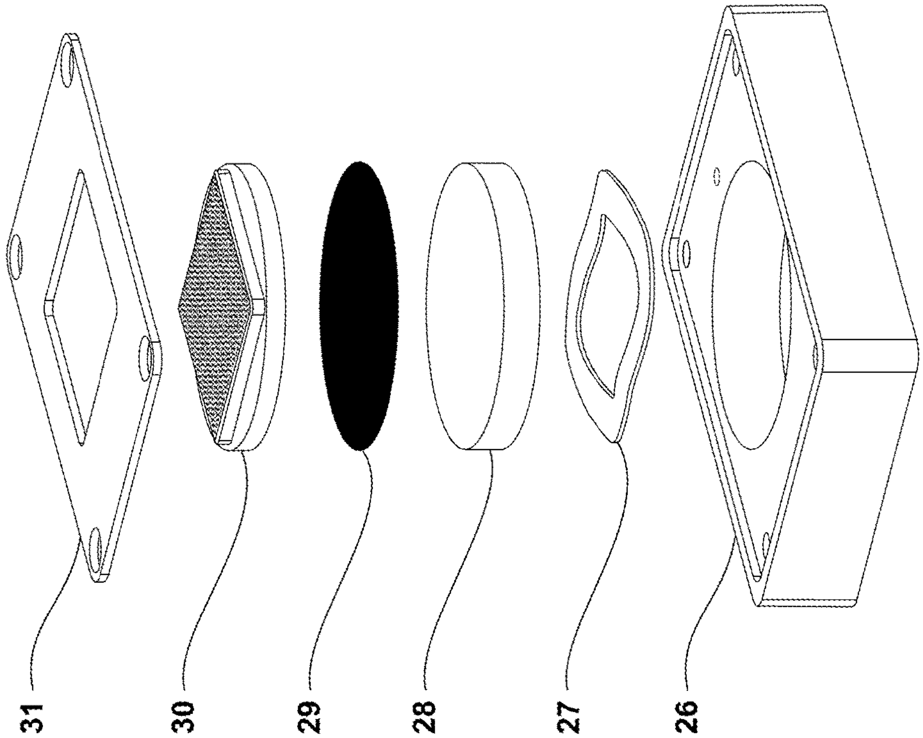
FIG. 5A is an exploded view of propellant module.

A non-limiting example of a propellant module is shown in FIGS. 5A-5C. In this example all of the components which are in contact with the propellant are stored in a single drop-in module which isolates the propellant from the rest of the system while allowing for easy replacement when running the thruster multiple times or with different propellants. The components of the propellant module are shown in FIG. 5A, which consist of a module housing 26, compression spring 27, porous propellant reservoir 28, hydraulic interface layer 29, emitter array 30, and distal electrode 31. In FIG. 5B, an opening for high voltage connection pin 32 and a pump-out hole 33 are shown. In FIG. 5C, exposed emitters 34 are shown.

EXAMPLES

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example 1—Synthesis of 1-methyl-3-[3-(1H,1H,2H,2H-perfluorodecylthio)propyl]imidazolium bis(trifluoromethylsulfonyl)azanide. To a 20 mL scintillation vial equipped with a magnetic stir bar was added 2.6 mmol of 1-methyl-3-(2-propen-1-yl)imidazolium bis(trifluoromethylsulfonyl)azanide, 5.2 mmol (2.5 g) 1H,1H,2H,2H-perfluorodecanethiol, and 0.07 mmol (33 mg) DMPA. Ten mL of a 1:1 v/v mixture of DCM:MeOH was added, the mixture capped, and then stirred until complete dissolution of the solids. The mixture was subject to broadband UV irradiation (centered at 365 nm) for 1 hr. with stirring. After irradiation, the reaction mixture was transferred to a round bottom flask and solvent was removed via rotary evaporation. Then, 50 mL hexanes were added to the solids and heated with stirring for 1 hr. The mixture was allowed to come to room temperature, the hexanes decanted, and washed twice more with 50 mL hexanes. The product was subject to a vacuum line ($10^{-2}$ torr) to remove residual solvent. The synthesis product was analyzed by nuclear magnetic resonance (NMR) spectroscopy, Fourier-transform infrared spectroscopy (FTIR), and high-resolution mass spectrometry (HRMS) techniques and found to be the expected product with a neutral mass of 883 amu.

Example 2—Synthesis of 1,3-bis[3-(1H,1H,2H,2H-perfluorodecylthio)propyl]imidazolium bis(trifluoromethylsulfonyl)azanide. The procedure of Example 1 was used except 1-methyl-3-(2-propen-1-yl)imidazolium bis(trifluoromethylsulfonyl)azanide was substituted for 1,3-bis(2-propen-1-yl)imidazolium bis(trifluoromethylsulfonyl)azanide and the concentration of this substituted material was halved to maintain a concentration of 2.6 mmol ene. The resulting synthesis yielded 1,3-bis[3-(1H,1H,2H,2H-perfluorodecylthio)propyl]imidazolium bis(trifluoromethylsulfonyl)azanide. The synthesis product was analyzed by nuclear magnetic resonance (NMR) spectroscopy, Fourier-transform infrared spectroscopy (FTIR), and high-resolution mass spectrometry (HRMS) techniques and found to be the expected product with a neutral mass of 1389 amu.

Example 3—Synthesis of 1-methyl-3-[2,3-bis(1H,1H,2H,2H-perfluorodecylthio)propyl]imidazolium bis(trifluoromethylsulfonyl)azanide. The procedure of Example 2 was used except 1-methyl-3-(2-propen-1-yl)imidazolium bis(trifluoromethylsulfonyl)azanide was substituted for 1-methyl-3-(2-propyn-1-yl)imidazolium bis(trifluoromethylsulfonyl) azanide. The resulting synthesis yielded 1-methyl-3-[2,3-bis (1H,1H,2H,2H-perfluorodecylthio)propyl]imidazolium bis (trifluoromethylsulfonyl)azanide. The synthesis product was analyzed by nuclear magnetic resonance (NMR) spectroscopy, Fourier-transform infrared spectroscopy (FTIR), and high-resolution mass spectrometry (HRMS) techniques and found to be the expected product with a neutral mass of 1362 amu.

Example 4—Synthesis of 3,3'-(1,10-decanediyl)bis-1,1'-[3-(1H,1H,2H,2H-perfluorodecylthio)propyl]imidazolium bis(trifluoromethylsulfonyl)azanide. The procedure of Example 2 was used except 1-methyl-3-(2-propen-1-yl) imidazolium bis(trifluoromethylsulfonyl)azanide was substituted for 3,3'-(1,10-decanediyl)bis-1,1'-(2-propen-1-yl) imidazolium bis(trifluoromethylsulfonyl)azanide. The resulting synthesis yielded 3,3'-(1,10-decanediyl)bis-1,1'-[3-(1H,1H,2H,2H-perfluorodecylthio)propyl]imidazolium bis (trifluoromethylsulfonyl)azanide. The synthesis product was analyzed by nuclear magnetic resonance (NMR) spectroscopy, Fourier-transform infrared spectroscopy (FTIR), and high-resolution mass spectrometry (HRMS) techniques and found to be the expected product with a neutral mass of 1877 amu.

Example 5—Synthesis of 3,3'-(1,2-ethanediyl)bis-1,1'-[3-(1H,1H,2H,2H-perfluorodecylthio)propyl]imidazolium bis (trifluoromethylsulfonyl)azanide. The procedure of Example 2 was used except 1-methyl-3-(2-propen-1-yl) imidazolium bis(trifluoromethylsulfonyl)azanide was substituted for 3,3'-(1,2-ethanediyl)bis-1,1'-(2-propen-1-yl)imidazolium bis(trifluoromethylsulfonyl)azanide. The resulting synthesis yielded 3,3'-(1,2-ethanediyl)bis-1,1'-[3-(1H,1H,2H,2H-perfluorodecylthio)propyl]imidazolium bis(trifluoromethylsulfonyl)azanide. The synthesis product was analyzed by nuclear magnetic resonance (NMR) spectroscopy, Fourier-transform infrared spectroscopy (FTIR), and high-resolution mass spectrometry (HRMS) techniques and found to be the expected product with a neutral mass of 1765 amu.

Example 6—Process of Making a Thruster. Referring to FIGS. 2A and 2C, the thruster housing 9 may be fabricated easily on a CNC mill. The preferred choice of material is aluminum, though other conductive materials would also be acceptable. The most important consideration in fabricating the thruster housing is to ensure that the distance between the propellant module 8 and the extractor mounting points be accurately machined and consistent to within approximately 1 thousandth of an inch to ensure the final assembled emitter to extractor separation 11 is precisely controlled. In certain embodiments, shims may be placed between the propellant module 8 and the thruster housing 9 to precisely tune this parameter. Care should also be taken to ensure any high voltage connections be properly electrically isolated to the intended operated voltage (typically several thousand volts).

Fabrication of a high-density electrospray extractor electrode has previously been accomplished only through expensive and difficult techniques such as laser cutting, chemical etching, or additive manufacturing. Two possible configurations for extractor electrodes have been discussed here; a one-piece design shown in FIGS. 3A-3D and a two-piece design shown in FIGS. 4A-4D. Referring to FIGS. 3A-3C, for the one-piece design a flat sheet of conductive metal such as stainless steel, titanium, or molybdenum may be used 13 and 17. The thickness of the metal depends on design preference, but should be thick enough to provide rigidity and flatness over its length. The difficulty in manufacturing this component is that the active thrust area 14 and 18 is ideally as thin and flat as possible (typically less than a few thousandths of an inch), while having the largest holes 15 possible (ideally 20 thousandths of an inch or larger). In order to accomplish this on a conventional CNC mill several steps are carefully followed.

FIGS. 7A-7F depict a method of extractor electrode fabrication. First, a fixture is built in which the top surface is flat to approximately 1 thousandth of an inch and there exists enough tapped holes to securely mount a flat plate with dimensions larger than the intended final extractor electrode 39. Second, the material chosen for the extractor electrode 40 as well as a rigidity plate 41 is roughly cut out to dimensions larger than the final intended extractor electrode dimensions. The rigidity plate may be made of any easily machined material and is thick enough to be rigid over its entire length. For the embodiment shown here, 0.05 inch thick aluminum is used. Once prepared, the extractor sheet and rigidity plate are glued together 42 using an adhesive which is readily dissolved with an available solvent. In the example shown, a cyanoacrylate glue which may be dissolved in acetone is used. This process ensures that minimal stretching and vibration of the extractor material occur during the sensitive machining process discussed below. Once glued, outer mounting holes are drilled through the assembly and the assembly is then bolted to the corresponding holes in the electrode fixture with the extractor material on top 43. The fixture is desirably then mounted in a vice on a CNC mill.

With the bonded sheets securely bolted to the fixture and in a vice on a CNC mill, the extractor electrode can now be machined. Inner holes, which will serve as the mounting holes of the final extractor electrode, are drilled through both sheets, with bolts then used to secure the inner region of the plates to the fixture. Next, the active thrust area is desirably machined to be as thin as possible by carefully milling the material to create a pocket in the extractor sheet with the desired active thrust area dimensions 44. This is where all of the previous steps become important, as without the extremely flat and stable surfaces provided by the fixture and adhesive the metal will inevitably tear as the thickness is reduced to the required few thousandths of an inch. Proper CNC settings for the chosen material will also be important because the metal will have a tendency to stretch as it is thinned, and while some stretching is acceptable, excessive stretching will lead to variability in the extractor flatness which may compromise thruster performance. Once the active thrust area pocket 44 is complete, the edges may be optionally chamfered for additional ion clearance 45.

With the active thrust area finished the extractor holes 46 are may now be drilled. For optimal thruster operation, the extractor holes are desirably located to better than 1 thousandth of an inch. While typical CNC mills are capable of such precision, the thin material will tend to be pulled by the drilling operation, resulting in slight variations in hole position. For this reason, this operation relies on the previously described fixture and bonding technique to be successful, particularly if high emitter density, and therefore extractor hole density, is required. The more uniformly bonded the extractor material is to the rigidity plate, the better the hole localization. While this operation has been successfully using spindle revolutions per minute (RPM) as low as 5,000 RPM, it has been found that best results are obtained when using a high-speed spindle at 50,000 RPM. In the embodiment shown, 576 holes with center-to-center distances of 0.0215 inches and diameters of 0.02 inches have been used.

Once the extractor holes have been drilled, the outer electrode profile 47 may be milled. Once this is complete the two pieces of material may be removed from the fixture and submerged in a chemical bath appropriate to the adhesive used to bond the pieces together. After the adhesive has dissolved, the two pieces should easily separate, revealing the finished one-piece extractor electrode as shown in FIG. 3A.

The two-piece extractor electrode requires many of the same steps as described above, however the machining is somewhat simpler since it does not require the active thrust area to be machined down. For this embodiment, the chosen extractor material may be purchased already at the desired thickness (ideally a few thousandths of an inch). The material is again bonded to a rigidity plate and placed in the fixture as described above to ensure the holes are well-localized. In this case a frame is fabricated separately from the grid out of thicker conductive material such as stainless steel, titanium, or molybdenum. Once completed, the extractor grid and the frame are bonded together using a space-rated low outgassing adhesive such as Eccobond 56C. Care is taken to ensure that the thin extractor grid material be uniformly bonded to the frame to ensure no droop under gravity or electrostatic forces and minimal deviation from flatness. An example of a finished two-piece extractor electrode is shown in FIG. 4A.

Referring to FIG. 5A, aside from the emitters 30 and reservoir 28, the components that make up the propellant module do not require any special machining techniques, however a few considerations should be noted. The propellant module housing 26 is desirably constructed from a material with minimal outgassing properties and the thickness and dielectric strength of the chosen material is sufficient to electrically isolate up to the desired thruster operation voltage without dielectric breakdown. In the embodiment shown, polyether ether ketone (PEEK) is used. Additionally, the distal electrode 31 should be made from a conductive metal such as stainless steel, titanium, or molybdenum, provided it is chemically compatible with the chosen ionic liquid, and should be thick enough to compress the other components within the propellant module against the spring 27 without deforming. Finally, the hydraulic interface 29 may be made from any compatible porous material with a pore size larger than that of the emitters. For the embodiment of FIG. 5A, Whatman qualitative grade 1 filter paper with a pore size of 11 micrometers is used.

With all of the components fabricated, the components should be cleaned with ethyl alcohol and allowed to dry to ensure vacuum compatibility and minimal debris on the porous surfaces. The propellant module would then be assembled as shown in FIG. 5A. Referring to FIG. 2A, once assembled, the propellant module 8 is mounted within the thruster housing 9. At this point it is important to accurately measure the heights between the extractor electrode mounting points on the thruster housing and the tips of the emitters. These measurements can be done to better than one thousandth of an inch using a digital optical microscope. It is also a good idea to measure any deformation in flatness on the bottom of the extractor grid so that the most accurate estimate of the distance between the extractor and the emitters can be obtained. This distance should be as small as possible for best performance. If the distance is greater than a few thousands of an inch then shims may be used beneath the propellant module to optimize it.

With the propellant module installed and properly positioned, the thruster is ready be loaded with the chosen ionic-liquid propellant. The preferred method of loading is to first place the appropriate volume of ionic liquid in a vacuum chamber and pump on it for a few hours at pressures less than around 10^-5 Torr to remove any adsorbed water or other high vapor pressure contaminants. The thruster is then placed in the vacuum environment and the outgassed propellant slowly dripped directly onto the emitter layer. Loading under vacuum is preferred since it promotes filling of the pores and prevents additional water from adsorbing onto the propellant and debris from contaminating the emitters. Referring to FIG. 5A, the loaded propellant will slowly work its way through the pores of the emitter array 30, through the interface layer 29, and into the reservoir 28. In one aspect, while the emitter array and interface layer are fully saturated with propellant, the reservoir is only partially filled. The reason for this is to allow some negative Laplace pressure to exist which results in smaller Taylor cones and therefore lower risk of the conductive ionic liquid shorting the emitter array to the extractor electrode.

Referring to FIG. 2A, with the propellant loaded into the porous material, the thruster may be removed from vacuum and the extractor grid 7 aligned and installed. This process may be done while viewing under a digital optical microscope. It is desirable that the grid apertures be properly aligned with the emitters so as to minimize grid interception and therefore limit mechanisms which may lead to premature thruster failure, such as the formation of ionic-liquid bridges between the emitters and extractors. The assembled thruster is best stored under vacuum or in a dry nitrogen environment to limit water and other contaminants from adsorbing onto the ionic-liquid.

Proper operation of the thruster typically requires for it to be placed in a low pressure environment of no more than 10^-5 Torr. The preferred electrical connections are to wire the emitters to a high voltage power supply or amplifier capable of at least 3,000 volts and connect the extractor electrode to ground. However, wiring the emitters to ground and biasing the extractor electrode is also acceptable. If bipolar operation is intended, then a bipolar power supply or amplifier will be needed. When connected in the preferred manner, biasing the emitters to a positive voltage will result in positive ion emission, while a negative bias will result in negative ion emission.

Initial start-up of the thruster is typically done by slowly raising the applied voltage until indications of emission are seen, such as the power supply sourcing current to maintain the applied voltage. The voltage required for emission depends on several factors such as propellant type, extractor-emitter separation, emitter sharpness, extractor hole size, and reservoir pore size, but ideally may start as soon as 1000 volts. Raising the voltage further after initial emission will result in higher current emission (and therefore thrust), however higher voltages and emission currents may lead to premature thruster failure. Typical reasonable operating voltages are within 500 to 700 volts of the start-up voltage.

Example 7—Process of Making an Emitter Array. Fabrication of a high density discrete emitter array has previously only been accomplished through high cost and time-consuming microfabrication techniques. The ability to conventionally machine such a component as described here allows for significantly more rapid prototyping for research and development, as well as reducing the cost of thruster fabrication to levels which make it economically feasible for high performance propulsion systems to be installed on small satellites in which limited budget is available. The disclosed technique can also be used advantageously to fabricate emitter arrays having lower densities as the technique is efficient for fabricating arrays in general.

An emitter array can be fabricated from porous borosilicate glass, for example, porous borosilicate glass with a pore size smaller than that of the reservoir and hydraulic interface. Here by example, the minimum pore size of the emitter glass is 1 micrometer. The fabrication technique used is schematically shown in FIGS. 8A-8F. First a fixture is built to fix the glass disk in place during machining FIG. 8A. The fixture shown consists of a circular pocket 48 with a diameter of a few thousandths of an inch larger than the chosen glass disk diameter, a slot down the center 49, a larger square region on top 50 and a smaller square region on bottom 51. With the glass disk placed in the circular pocket, the fixture is then placed in a vice on a CNC mill with the center slot oriented such that parallel with the vice jaws. As the vice jaws are tightened the larger top section of the fixture will compress around the glass disk, thus safely fixing it in place. Typically, the fixture is built to sufficiently high precision that the glass disk is held flat to within approximately a thousandth of an inch.

Figure 8A:
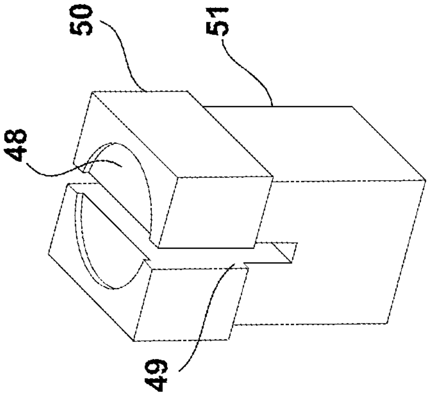
FIG. 8A is an isometric view of an emitter fixture.
Figure 8B:
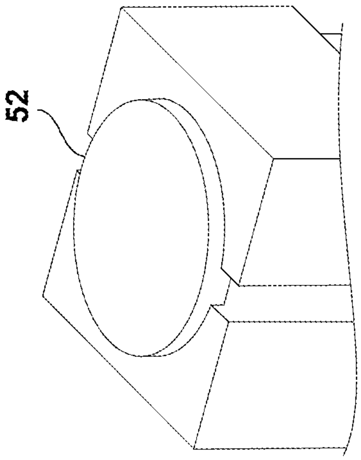
FIG. 8B is an isometric view of a borosilicate glass material in an emitter fixture.
Figure 8C:
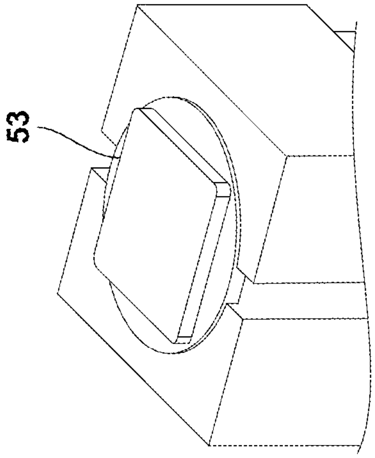
FIG. 8C is an isometric view of a borosilicate glass material having a first platform machined into the borosilicate glass material.
Figure 8D:
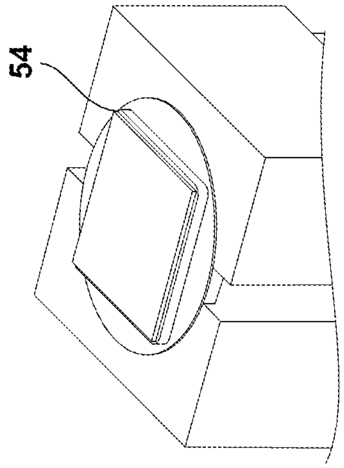
FIG. 8D is an isometric view of a borosilicate glass material having a second platform machined into the borosilicate glass material.

With the disk fixed in the fixture the fabrication of the emitter array may begin. Referring to FIG. 8B, using the CNC mill, both the top and bottom surfaces of glass work piece are faced to ensure flatness, and the outer circular perimeter cut to result in the glass work piece accurately fitting within the propellant module housing. Referring to FIG. 8C, next a square profile is milled in the glass work piece to produce an elevated emitter plane 53 which will sit above the distal electrode 31 (of FIG. 5A) after the propellant module is assembled. Referring to FIG. 8D, depending on the chosen geometry, an additional square profile 54 may be optionally milled around the emitter plane to ensure no partially cut emitters reside on the furthest edges of the final emitter array.

Figure 6A:
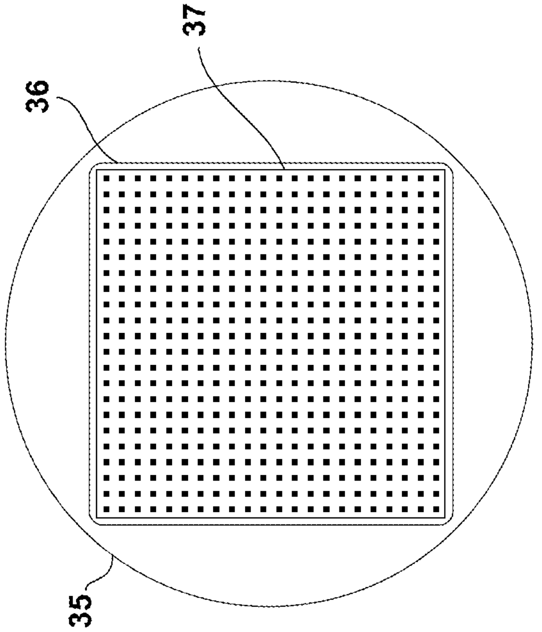
FIG. 6A is a top view of emitter array.
Figure 6B:
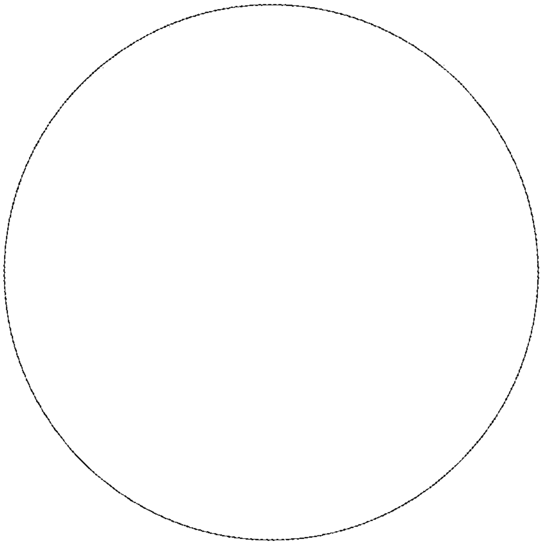
FIG. 6B is a bottom view of emitter array.
Figure 6C:
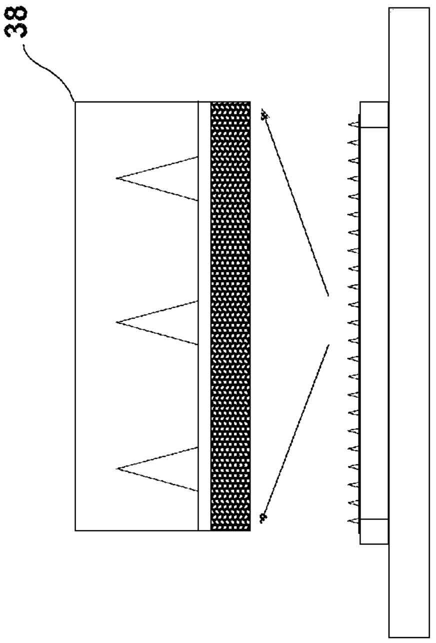
FIG. 6C is a side profile of emitter array.
Figure 6D:
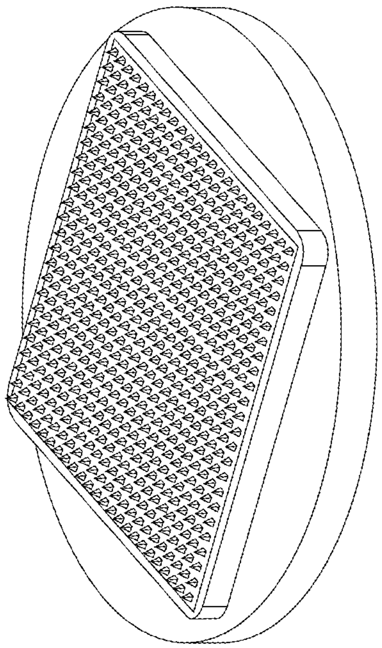
FIG. 6D is an isometric view of an emitter array.
Figure 7A:
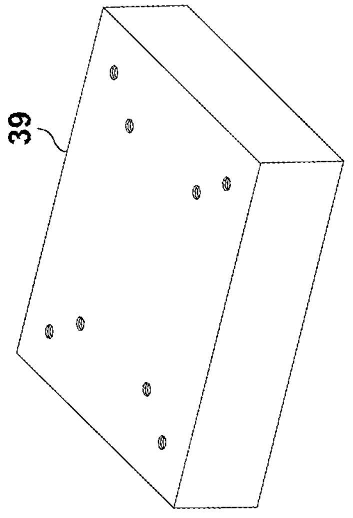
FIG. 7A is an isometric view of an extractor electrode fixture.
Figure 7B:
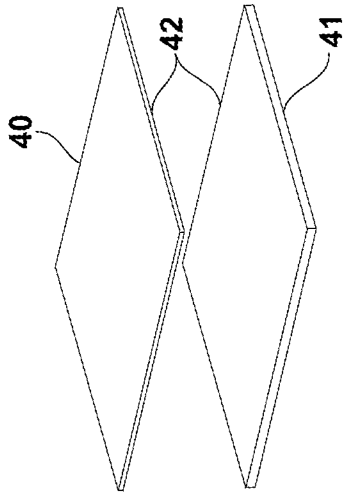
FIG. 7B is an isometric view of extractor electrode material and rigidity plate.
Figure 7C:
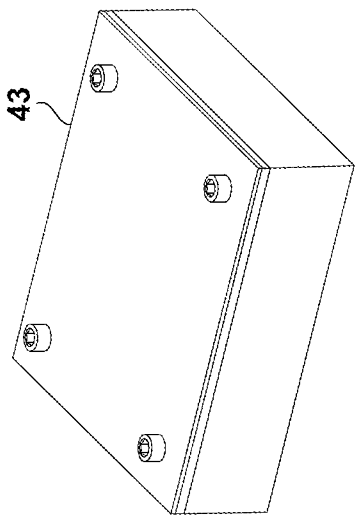
FIG. 7C is an isometric view of an extractor electrode material and rigidity plate mounted to fixture.
Figure 7D:
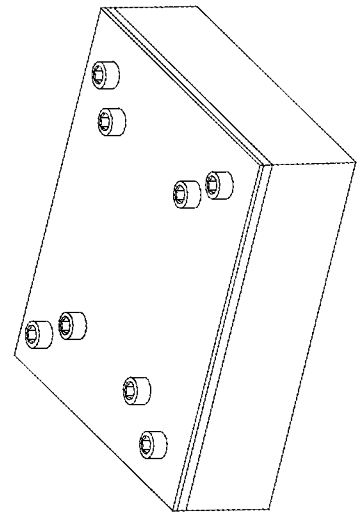
FIG. 7D is an isometric view of an extractor electrode fixture having additional mounting points.
Figure 7E:
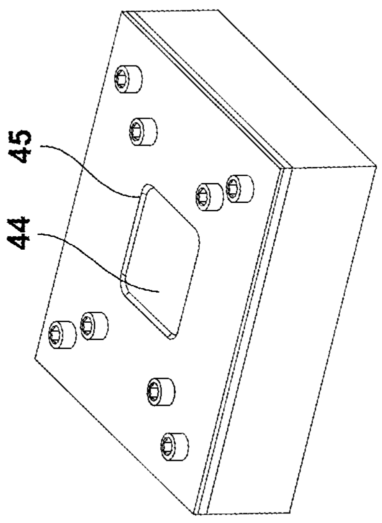
FIG. 7E is an isometric view of an active thrust area machined into extractor electrode.
Figure 7F:
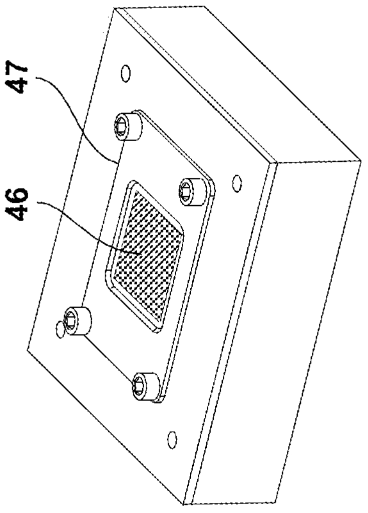
FIG. 7F is an isometric view of a completed extractor electrode in an extractor electrode fixture.
Figure 8E:
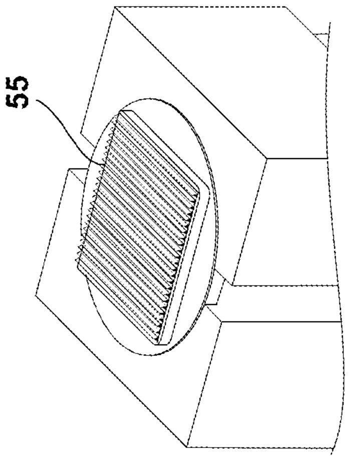
FIG. 8E is an isometric view of a borosilicate glass material having a first set of machined channels.
Figure 8F:
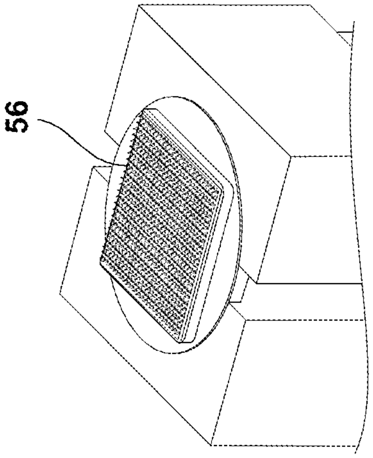
FIG. 8F is an isometric view of a borosilicate glass material having a second set of machined channels that are perpendicular to a first set of machined channels.

The glass work piece is now ready to have the emitters machined. For this operation a miniature tapered square end mill which has a flat tip and a tapered cutting surface is used. The specific taper angle and flat tip diameter determines the shape and maximum density of emitters. Thus, such parameters are chosen for a particular design. While functional emitter arrays have been fabricated using spindle speeds as low as 5,000 RPM, it has been found that significantly sharper emitter tips may be built when using a high-speed spindle at 50,000 RPM. Referring to FIG. 8E, using the CNC mill, channels are cut through the glass with the depth and distance between each channel chosen so that the tapered end mill cutting surface overlaps at the glass surface, thus forming linear prisms across the active thrust area 55. Referring to FIG. 8F, as a final step, the previous operation may be repeated in the orthogonal direction, thus forming discrete emitter structures throughout the active thrust area 56. For the embodiment shown here, emitter heights of 0.012 inches and separations of 0.0215 inches are used, resulting in 576 emitters over a 0.5 inch by 0.5 in square active thrust area. However, emitter arrays with separations as small as 0.0143 inches can be successfully fabricated using this technique, resulting in over 750 emitters per square centimeter. An example of an emitter array produced by the present process is shown in FIGS. 6A-6D. FIG. 6A is a top view of emitter array showing porous borosilicate glass disk 35 having emitter platform 36 and emitters 37. FIG. 6B is a bottom view of emitter array. FIG. 6C is a side profile of emitter array showing emitter profiles 38 and FIG. 6D is an isometric view of an emitter array.

While the embodiment shown here shows the fabrication of discrete emitter tips, electrospray thrusters using linear emitters are also functional. It should be noted that the process described here allows significantly higher density of linear emitters to be fabricated than the referenced method simply by omitting the final step in the above process 55 of FIG. 8E. If these linear emitter are combined with an extractor grid with slots rather than individual holes, a high density linear emitter electrospray thruster can be obtained.

As a final component, the embodiment of the reservoir 28 of FIG. 5A is constructed out of porous borosilicate glass with a pore size larger than that of the emitters. In the example shown, the minimum pore size is 16 micrometers. Fabrication of the reservoir is done by using the above emitter fixture and simply facing and circularizing both sides of the glass disk as in 52 of FIG. 8B.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A thruster propellant comprising a plurality of cations and an anions and having an overall net zero charge, said cation comprising one or more heads, and one or more hydrophobic fluorinated tails that comprise one or more sulfur atoms, said sulfur atoms being separated from said fluorination and said head group by at least one carbon, said one or more tails being covalently bound to said one or more heads, each of said one or more heads being independently selected from the group consisting of an imidazolium, an imidazolinium, a phosphonium, an ammonium, a sulfonium, a pyridinium, a pyrrolidinium.

2. The thruster propellant of claim 1 wherein each of said one or more tails is independently an aliphatic moiety connected to one or more sulfur atoms which are each then connected to a partially hydrogenated fluorinated carbon chain.

3. The thruster propellant of claim 2 wherein each of said one or more tails is independently selected from the group consisting of tails having Formula 1 or Formula 2 below wherein:

a) S is sulfur;
b) F is fluorine;
c) X is hydrogen or fluorine;
d) the indice a is an integer from 0 to 20;
e) the indice b is an integer from 1 to 10;
f) the indice c is an integer from 1 to 18;
g) the indice d is an integer from 1 to 14; and
h)  represents an attachment point for Formulas 1 and 2 below to the thruster propellant Formula 1

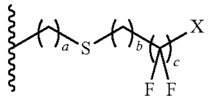

Formula 2

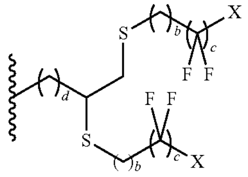

4. The thruster propellant of claim 3 wherein for Formula 1 and Formula 2 the indice a is an integer from 2 to 12; the indice b is an integer from 1 to 8; the indice c is an integer from 1 to 8; and the indice d is an integer from 1 to 10.

5. The thruster propellant of claim 4 wherein for Formula 1 and Formula 2 the indice a is an integer from 2 to 4; the indice b is an integer from 1 to 3; the indice c is an integer from 6 to 8; and the indice d is an integer from 1 to 4.

6. The thruster propellant of claim 1 comprising one or more organic linking groups that link one or more of said one or more heads.

7. The thruster propellant of claim 6, wherein each of said one or more linkers is independently selected from the group consisting of aliphatic, aromatic, poly(ether), (poly)thio (ether), and isocyanurate.

8. The thruster propellant of claim 3, said thruster propellant comprising a material selected from Formulas 3 through 14 below and mixtures thereof:

wherein for each of Formulas 3 through 14:

a) each anion A is independently selected from the group consisting of tetrafluoroborate, hexafluorophosphate, and bis(trifluoromethylsulfonyl)azanide;

b) each $R_1$ is independently selected from the group consisting of: hydrogen; Formula 1 wherein the indice a is an integer from 1 to 20; Formula 2; a $C_1$-$C_{12}$ branched alkane; a $C_1$-$C_{12}$ linear alkane; a substituted aromatic moiety; or an unsubstituted aromatic moiety;

c) each $R_2$, $R_3$ and $R_4$ is independently selected from the group consisting of, hydrogen; Formula 1; Formula 2; a $C_1$-$C_{12}$ branched alkane; a $C_1$-$C_{12}$ linear alkane; a substituted aromatic moiety; or an unsubstituted aromatic moiety;

d) each $R_5$ is independently selected from the group consisting of: hydrogen; Formula 1 wherein the indice a is an integer from 1 to 20; a $C_1$-$C_{12}$ branched alkane; a $C_1$-$C_{12}$ linear alkane; a substituted aromatic moiety; and an unsubstituted aromatic moiety;

Formula 3

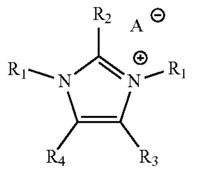

Formula 4

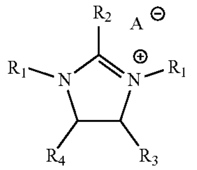

Formula 5

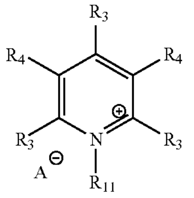

Formula 6

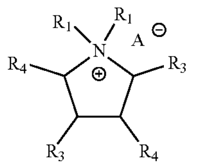

Formula 7

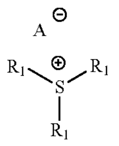

Formula 8

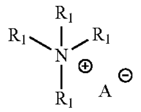

Formula 9

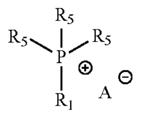

-continued

Formula 10

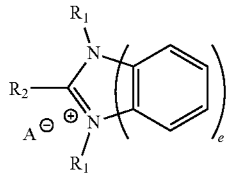

Formula 11

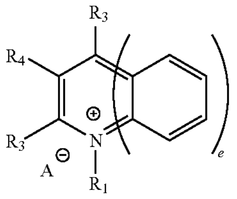

Formula 12

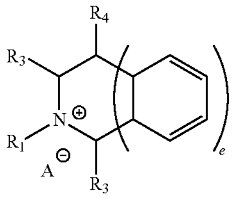

Formula 13

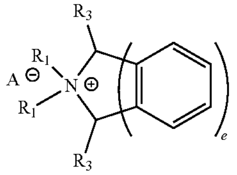

Formula 14

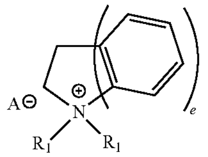

9. The thruster propellant of claim 8 wherein:

a) for $R_1$ said substituted aromatic moiety is a substituted benzene moiety and said unsubstituted aromatic moiety is a benzene moiety;

b) for $R_2$, $R_3$ and $R_4$, said substituted aromatic moiety is a substituted benzene moiety and said unsubstituted aromatic moiety is a benzene moiety, with the proviso that for Formula 3, Formula 5 and Formula 6, adjacent $R_3$ and $R_4$ moieties can be one or more benzo moieties rather than single independent moieties; and c) for $R_5$ said substituted aromatic moiety is a substituted benzene moiety and said unsubstituted aromatic moiety is a benzene moiety.

10. The thruster propellant of claim 8 wherein Formula 3's $R_1$ through $R_4$ groups are selected from the following sets:

a) moiety Set 1 wherein:
  (i) the $R_1$ adjacent to $R_4$ is methyl;
  (ii) the $R_1$ adjacent to $R_3$ is a tail having Formula 1 wherein the indice a is 3, the indice b is 2 and the indice c is 8, X is fluorine; and
  (iii) $R_2$, $R_3$ and $R_4$ are hydrogen;

b) moiety Set 2 wherein:
  (i) each $R_1$ is a tail having Formula 1 wherein the indice d is 1, the indice b is 2 and the indice c is 8, X is fluorine; and
  (ii) $R_2$, $R_3$ and $R_4$ are hydrogen;

c) moiety Set 3 wherein:
  (i) the $R_1$ adjacent to $R_4$ is methyl;
  (ii) the $R_1$ adjacent to $R_3$ is a tail having Formula 2 wherein the indice d is 1, the indice b is 2 and the indice c is 8, X is fluorine; and
  (iii) $R_2$, $R_3$ and $R_4$ are hydrogen;

d) moiety Set 4 wherein:
  (i) the $R_1$ adjacent to $R_3$ is formula has Formula 15 below wherein the indice f is 10 and $R_6$ is a tail having Formula 1 wherein for Formula 1, the indice a is 3, the indice b is 2 and the indice c is 8, X is fluorine Formula 15

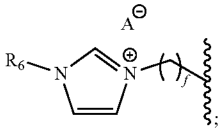

(ii) the $R_1$ adjacent to $R_4$ is a tail having Formula 1 wherein the indice a is 3, the indice b is 2 and the indice c is 8, X is fluorine; and
  (iii) $R_2$, $R_3$ and $R_4$ are hydrogen;

e) $R_1$ through $R_4$ moiety Set 5 wherein:
  (i) the $R_1$ adjacent to $R_3$ has Formula 15 below wherein the indice f is 2 and $R_6$ is a tail having Formula 1 wherein for Formula 1, the indice a is 3, the indice b is 2 and the indice c is 8, X is fluorine Formula 15

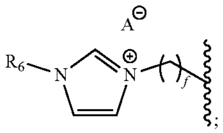

(ii) the $R_1$ adjacent to $R_4$ is a tail having Formula 1 wherein the indice a is 3, the indice b is 2 and the indice c is 8, X is fluorine; and
  (iii) $R_2$, $R_3$ and $R_4$ are hydrogen.

11. A space craft comprising a thruster and a thruster propellant according to claim 1.

12. A space craft according to claim 11, said space craft being selected from a satellite or a space station.

* * * * *